United States Patent [19]

Fisher et al.

[11] 4,230,726

[45] Oct. 28, 1980

[54] CONTROL OF PARASITIC MITES WITH ALKYL AMINES

[75] Inventors: William F. Fisher, Kerrville, Tex.; Malcolm J. Thompson, Baltimore, Md.; Fred C. Wright, Kerrville, Tex.; William E. Robbins, Silver Springs, Md.

[73] Assignee: The United States of America as represented by the Secretary of Agriculture, Washington, D.C.

[21] Appl. No.: 53,475

[22] Filed: Jun. 29, 1979

[51] Int. Cl.³ .................... A01N 33/02; A01N 43/84; A01N 43/40; A01N 37/18
[52] U.S. Cl. .................... 424/325; 424/248.4; 424/267; 424/274; 424/285; 424/320
[58] Field of Search ............... 424/325, 320, 285, 274, 424/267, 248.4

[56] References Cited

U.S. PATENT DOCUMENTS

| | | | |
|---|---|---|---|
| Re. 20,869 | 10/1938 | Bousquet et al. | 424/325 |
| 2,166,119 | 7/1939 | Bousquet et al. | 424/320 |
| 3,758,516 | 9/1973 | Siddall et al. | 424/267 |
| 4,036,987 | 7/1977 | Thompson et al. | 424/325 |
| 4,073,939 | 2/1978 | Thompson et al. | 424/320 |

FOREIGN PATENT DOCUMENTS 769052 12/1971 Belgium ........................... 424/325

*Primary Examiner*—Douglas W. Robinson
*Attorney, Agent, or Firm*—M. Howard Silverstein; William E. Scott; David G. McConnell

[57] ABSTRACT

Certain secondary and tertiary straight and branched chain amines and amides are found to be highly effective for controlling scabies mites and other parasitic mites.

5 Claims, No Drawings

CONTROL OF PARASITIC MITES WITH ALKYL AMINES

BACKGROUND OF THE INVENTION

1. Field of the Invention

This invention relates to the control of scabies mites and other parasitic mites and more specifically to the control of these parasites with certain straight and branched-chain amines and amides.

2. Description of the Art

A particular shortcoming in the control of scabies mites in livestock is the fact that at present there are only four chemicals registered with the Environmental Protection Agency for use in the United States as dips on cattle and sheep. Although the four chemicals are effective in the control of scabies, their use presents certain disadvantages. Three of the chemicals, toxaphene, coumaphos, and phosmet, cannot be used on lactating dairy cattle and beef cattle treated with phosmet and toxaphene must be held 21 and 28 days, respectively, before slaughter to avoid pesticide residue problems. In fact, toxaphene, one of the most widely used agricultural insecticides in the world, has been found by the National Cancer Institute to cause liver cancer in male and female mice (Chemical and Engineering News, Volume 57, No. 12, March 19, 1979, page 20). The fourth chemical, lime-sulfur, which is used on lactating dairy cattle must be heated to 95° to 105° F. to be effective.

Some of the compounds of the present invention are also useful in the control of nematodes and other helminths, U.S. Pat. No. 4,036,987 and No. 4,073,939.

SUMMARY OF THE INVENTION

An object of this invention is to provide new chemicals useful in the control of scabies mites and other parasitic mites.

Another object is to provide compounds that are lethal to scabies mites and other parasitic mites yet have relatively low vertebrate toxicities so that they are not toxic or harmful to the host.

A further object is to provide compounds that are lethal to scabies mites and other parasitic mites at concentrations equivalent to or far below those required for most of the currently used chemicals.

A still further object is to provide compounds that are economical to use for the control of scabies mites and other parasitic mites.

In general, according to this invention certain secondary and tertiary straight and branched chain amines and amides having chain lengths of from 8 to 24 carbon atoms are found to be highly effective for controlling scabies mites and other parasitic mites. Compounds found useful for the purpose of this invention are represented by the general formula

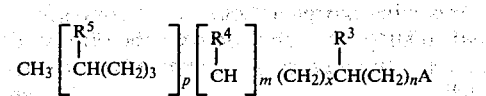

wherein A is selected from the group consisting of

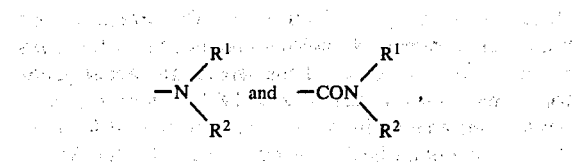

$R^1$ and $R^2$ are individually H, lower alkyl,

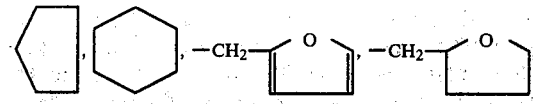

or taken together with the N is

x is a number from 5 to 17, n is a number from 1 to 5, m and p are individually H or lower alkyl.

More specifically, general formula 1 embodies the following types of compounds that have been found useful for the purposes of this invention

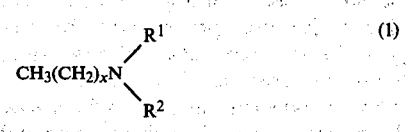

where $R^1$ and $R^2$ are the same as described under the general formula above and x is a number from 10 to 17;

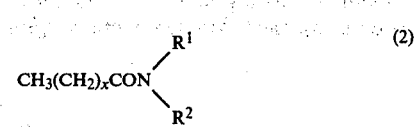

wherein $R^1$ and $R^2$ are individually lower alkyl and x is a number from 8 to 12; and

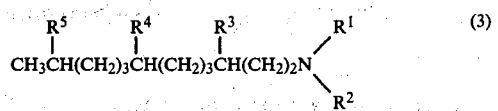

wherein $R^1$ and $R^2$ are as described under the general formula above and $R^3$, $R^4$, and $R^5$ are lower alkyl.

The term "lower alkyl" in this application refers to straight and branched chain saturated aliphatic hydrocarbons having a chain length of not more than four carbon atoms.

DESCRIPTION OF THE INVENTION

In 1975, parasitic mites causes an estimated $157 million loss to the United States livestock industry. Even though there were only 45 confirmed outbreaks of cattle scabies in the United States in 1975, approximately $65 million of this loss was due to psoroptic scabies in cattle. The problem has since increased in severity and in 1978 alone over 300 outbreaks of psoroptic scabies were confirmed in the United States.

Virtually all mammals including man suffer from parasitic mites and domestic animals, particularly livestock, are no exception. Psoroptic scabies of cattle are a universal problem; infestations have been and are today reported from all areas of the world. In recent years, following a violent outbreak in 1971, common scabies has become an ever increasing threat to the cattle industry and to animal health agencies in the United States. Consequently, in the United States, this disease must be reported to and is quarantined by the Veterinary Services of the Animal Plant Health Inspection Services of the U.S.D.A. With the distinct possibility that the use of certain of the more effective of these chemicals used for scabies mites control may be banned in the future, the need for new chemicals for control of scabies mites is even more urgent and critical.

The difficulty in finding safe active chemicals is partially responsible for the low number of registered compounds for control of scabies mites. Out of thousands of compounds tested in both government and industry evaluation programs, relatively few have been found to be both safe and effective against scabies mites and other parasitic mites. Consequently, it was very surprising and quite unexpected when we found that a number of N-substituted alkyl amines and amides of this invention displayed very high miticidal activity against scabies mites.

The compounds of the invention were prepared in 60–80% yield according to the general method of reaction of the appropriate acid with thionyl chloride to give the respective acid chloride which when reacted with the respective low molecular weight amine or ammonia yielded the amide which was reduced to the long chain or branched chain amine with lithium aluminum hydride in tetrahydrofuran. The amines could be in most cases purified via formation of the amine hydrochlorides and by reconversion to the free amines or by column chromatography. The outline of synthesis according to general known method is presented below.

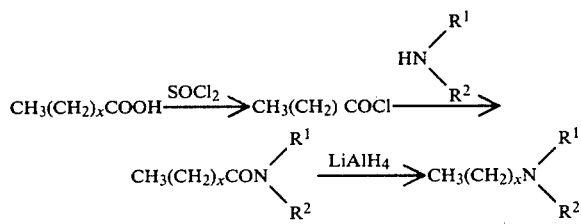

A typical preparation is illustrated by the following detailed example of the synthesis of N,N-dimethyl-dodecanamide [$CH_3(CH_2)_{10}CON(CH_3)_2$] and N,N-dimethyldodecanamine [$CH_3(CH_2)_{11}N(CH_3)_2$].

A mixture of 30 g of lauric acid (dodecanoic acid), 150 ml of dry benzene and 21.4 g (13.4 ml) of thionyl chloride was gently refluxed for about 16 hours. The solvent and excess thionyl chloride was removed to yield 32.8 g of the crude acid chloride. To a mechanically stirred solution of the crude acid chloride in 20 ml of dry hexane chilled to 10° C. was added 16 g of dimethylamine in 85 ml of hexane. The reaction mixture was removed from the ice bath, stirred for 2 hours at room temperature, and then filtered. The filtrate was concentrated to dryness under vacuum to give 32 g of crude N,N-dimethyldodecanamide, >95% pure. Trace amounts of the impurity dimethylamine hydrochloride were removed by partitioning the crude dimethylamide between hexane and water. The hexane phase was then dried over sodium sulfate and concentrated to dryness under vacuum, yielding >98% pure N,N-dimethyl-dodecanamide, $N_D19$ 1.4610.

Crude dimethylamide in 150 ml of dry tetrahydrofuran (THF) was added dropwise to a refluxing solution of 6 g of solid lithium aluminum hydride in 150 ml of THF, and the solution refluxed for about 16 hours, after which two drops of ethyl acetate were added to determine if an excess of lithium aluminum hydride was still present. The reaction mixture was chilled to 10° C., 25 ml of water added dropwise with caution, and then sodium hydroxide, 25 l g in 20 ml of water, was added. Upon standing for about 2 hours with occasional stirring and shaking, a a gelatinous mass formed and separated from the THF phase. The THF phase was removed and the gelatinous mass rinsed with additional THF. The THF phases were combined and concentrated nearly to dryness under vacuum. The residue was dissolved in hexane and the hexane solution washed with dilute sodium hydroxide, and with water, and then dried over sodium hydroxide pellets. The hexane solution (ca. 300 ml) was treated with a slight excess of a 6 N solution of hydrogen chloride in isopropanol to precipitate out amine hydrochloride which was collected by filtration. The amine hydrochloride was treated with a 3 N sodium hydroxide solution and the amine extracted into hexane. The hexane phase was washed with water, and then dried over sodium hydroxide pellets. Removal of the hexane under vacuum gave 25 g (98%) of N,N-dimethyldodecanamine, $n_D19$ 1.4463, >99% pure.

The compounds were tested in vitro on the rabbit ear mite, Psoroptes cuniculi, which has come to be used as the model biological system for testing candidate chemicals for miticidal activity against scabies mites such as the common scabies mite of cattle and sheep, Psoroptes ovis, and other parasitic mites. Groups of large mites (20 to 25 adults and nymphs) were exposed to the chemicals using a modification of the "tea bag" technique (J. Econ. Entomol. 65, 174, 1972), by dipping them for 30 seconds in aqueous emulsions prepared from a 10% emulsifiable concentrate (10% test chemical, 85% ethanol and 5% Triton X-100) of the test chemical. Triton X-100 is octylphenoxy polyethoxy ethanol, a nonionic surfactant containing an average of 8.5 ethylene oxide groups. Each compound was tested at a range of concentrations. At 24 hours after dipping, the mites were examined with the aid of a dissecting microscope, and those mites that showed absolutely no movement or that were able to move their legs but were unable to walk were judged as dead. Under these test conditions the range of concentrations required to kill 100% of the mites with three commercial miticide formulations used for scabies control, coumaphos, phosmet and toxaphene, are >0.1%, 0.005–0.01%, and 0.00005–0.0001% respectively. As shown in Table I, a surprisingly large number of the straight chain amines and amides of this invention were more active than the miticides that are currently registered for the control of the common scabies mite of cattle and sheep, with the exception of toxaphene, when tested against the rabbit ear mite Psoroptes cuniculi. Compounds 7,18 and 27 were the most active causing complete lethality at concentrations of 0.0005–1.001%, thus approaching the effectiveness of toxaphene. In addition, a number of other chemicals, including Compounds 5,6,8,9,14,15,19,20,22,24,28,31,32,33,34,35,36,41 and 42 were also highly effective and killed 100% of the rabbit ear mites in the dipping test at the 0.001–0.005% concentration range.

In addition to the straight chain amides and amines in Table I, a number of branched-chain amides and amines were also quite active. For example, N,N-dimethyl-3,7,11-trimethyl-dodecanamine caused 100% mortality on rabbit ear mites at concentrations of 0.005 to 0.01% in "tea bag" dipping tests.

Seven of the more active compounds listed in Table I were further tested in the "tea bag" dipping test against the common scabies mite of cattle and sheep, *Psoroptes ovis*, which is the most economically important scabies mite of domestic animals. As shown in Table II all seven chemicals were highly effective against the common scabies mite of cattle and sheep and killed 100% of the mites in the dipping test at the 0.001–0.005% concentration range. Five of the test chemicals, compounds 6,8,15,20, and 22, were equally active against the common scabies mite and the rabbit ear mite while compounds 7 and 18 were only slightly less active.

A number of amines were tested in vivo at a range of concentrations for miticidal activity against scabies mites and other parasitic mites using rabbits infested in both ears with the rabbit ear mite *Psoroptes cuniculi*. Both ears of each of the infested rabbit were treated with aqueous emulsions containing from 0.2% to 1.0% of the test compound prepared from a 10% emulsifiable concentrate (10% test compound, 85% ethanol, and 5% Triton X-100) of the test compound. Approximately 10–12.5 ml of the emulsion was poured into each ear of the rabbit and massaged into the scabs for 1 minute. The rabbits were examined with an otoscope at regular intervals after treatment to determine the effectiveness of the compounds and the examinations were terminated at 41 to 44 days after treatment. The results of the treatments were classified as follows: A=No reduction in number of mites or amount of scab, B=Initial reduction in number of mites or scab but mite population soon builds back up, C=Near complete elimination of mites and scab; mites not found until end of test, D=Complete elimination of mites and scabs. The results of these in vivo tests are shown in Table III. All the test chemicals showed some degree of miticidal activity against the ear canker mites at the concentrations tested, and only Compounds 1,9, and 16 did not cause complete elimination of the mites and scabs at 1.0%, the highest concentration used. Compound 3 was highly active and completely eliminated mites and scabs at a concentration of 0.50%. Compounds 4,5,7, and 8 were completely effective at a concentration of 0.75% and Compounds 2 and 6 completely eliminated the infestations at a concentration of 1.0%.

TABLE I

Range of concentrations of N-substituted amines and amides required to kill 100% of nymphs and/or adults of the rabbit ear mite (*Psoroptes cuniculi*) exposed for 30 seconds in "tea bag" dipping tests.

| Compound Number | Formula | Concentration (%) |
|---|---|---|
| 1 | $CH_3(CH_2)_8CH_2N(CH_3)_2$ | 0.01–0.05 |
| 2 | $CH_3(CH_2)_9CH_2N(CH_3)_2$ | 0.01–0.05 |
| 3 | $CH_3(CH_2)_{10}CH_2N(CH_3)_2$ | 0.005–0.01 |
| 4 | $CH_3(CH_2)_{11}CH_2N(CH_3)_2$ | 0.005–0.01 |
| 5 | $CH_3(CH_2)_{12}CH_2N(CH_3)_2$ | 0.001–0.005 |
| 6 | $CH_3(CH_2)_{13}CH_2N(CH_3)_2$ | 0.001–0.005 |
| 7 | $CH_3(CH_2)_{14}CH_2N(CH_3)_2$ | 0.0005–0.001 |
| 8 | $CH_3(CH_2)_{15}CH_2N(CH_3)_2$ | 0.001–0.005 |
| 9 | $CH_3(CH_2)_{16}CH_2N(CH_3)_2$ | 0.001–0.005 |
| 10 | $CH_3(CH_2)_8CON(CH_3)_2$ | 0.05–0.1 |
| 11 | $CH_3(CH_2)_9CON(CH_3)_2$ | 0.01–0.05 |
| 12 | $CH_3(CH_2)_{10}CON(CH_3)_2$ | 0.005–0.01 |
| 13 | $CH_3(CH_2)_{11}CON(CH_3)_2$ | 0.005–0.01 |
| 14 | $CH_3(CH_2)_{12}CON(CH_3)_2$ | 0.001–0.005 |
| 15 | $CH_3(CH_2)_{15}N(CH_3)C_2H_5$ | 0.001–0.005 |
| 16 | $CH_3(CH_2)_{14}NHC_2H_5$ | 0.005–0.01 |
| 17 | $CH_3(CH_2)_{15}NHC_2H_5$ | 0.01–0.05 |
| 18 | $CH_3(CH_2)_{11}N(CH_3)$–cyclohexyl | 0.0005–0.001 |
| 19 | $CH_3(CH_2)_{11}NH$–cyclohexyl | 0.001–0.005 |
| 20 | $CH_3(CH_2)_{11}N(CH_3)C_3H_7$ | 0.001–0.005 |
| 21 | $CH_3(CH_2)_9N(CH_3)C_4H_9$ | 0.005–0.01 |
| 22 | $CH_3(CH_2)_{10}N(CH_3)C_4H_9$ | 0.001–0.005 |
| 23 | $CH_3(CH_2)_{10}CH_2NHCH(CH_3)_2$ | 0.01–0.05 |
| 24 | $CH_3(CH_2)_{10}CH_2N(CH_3)CH(CH_3)_2$ | 0.001–0.005 |
| 25 | $CH_3(CH_2)_8CH_2N$–piperidinyl | 0.005–0.01 |
| 26 | $CH_3(CH_2)_9CH_2N$–piperidinyl | 0.005–0.01 |

TABLE I-continued

Range of concentrations of N-substituted amines and amides required to kill 100% of nymphs and/or adults of the rabbit ear mite (*Psoroptes cuniculi*) exposed for 30 seconds in "tea bag" dipping tests.

| Compound Number | Formula | Concentration (%) |
|---|---|---|
| 27 | $CH_3(CH_2)_{10}CH_2N$⟨piperidine⟩ | 0.0005–0.001 |
| 28 | $CH_3(CH_2)_{12}CH_2N$⟨piperidine⟩ | 0.001–0.005 |
| 29 | $CH_3(CH_2)_7CH_2N$⟨pyrrolidine⟩ | 0.01–0.05 |
| 30 | $CH_3(CH_2)_8CH_2N$⟨pyrrolidine⟩ | 0.005–0.01 |
| 31 | $CH_3(CH_2)_9CH_2N$⟨pyrrolidine⟩ | 0.001–0.005 |
| 32 | $CH_3(CH_2)_{10}CH_2N$⟨pyrrolidine⟩ | 0.001–0.005 |
| 33 | $CH_3(CH_2)_{11}CH_2N$⟨pyrrolidine⟩ | 0.001–0.005 |
| 34 | $CH_3(CH_2)_{12}CH_2N$⟨pyrrolidine⟩ | 0.001–0.005 |
| 35 | $CH_3(CH_2)_{13}CH_2N$⟨pyrrolidine⟩ | 0.001–0.005 |
| 36 | $CH_3CH(CH_2)_3-\underset{\underset{CH_3}{\|}}{CH}(CH_2)_3\underset{\underset{CH_3}{\|}}{CH}(CH_2)_2N$⟨pyrrolidine⟩ with leading $CH_3$ | 0.001–0.005 |
| 37 | $CH_3(CH_2)_9CH_2N$⟨morpholine, O⟩ | 0.01–0.05 |
| 38 | $CH_3(CH_2)_{10}CH_2N$⟨morpholine, O⟩ | 0.01–0.05 |
| 39 | $CH_3(CH_2)_{11}CH_2N$⟨morpholine, O⟩ | 0.01–0.05 |
| 40 | $CH_3(CH_2)_{12}CH_2N$⟨morpholine, O⟩ | 0.01–0.05 |
| 41 | $CH_3(CH_2)_8CH_2NHCH_2$—furan | 0.001–0.005 |

TABLE I-continued

Range of concentrations of N-substituted amines and amides required to kill 100% of nymphs and/or adults of the rabbit ear mite (*Psoroptes cuniculi*) exposed for 30 seconds in "tea bag" dipping tests.

| Compound Number | Formula | Concentration (%) |
|---|---|---|
| 42 | CH₃(CH₂)₁₀CH₂NHCH₂—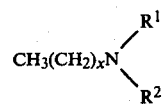 | 0.001–0.005 |
| 43 | CH₃(CH₂)₈CH₂NHCH₂—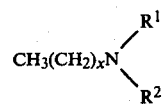 | 0.01–0.05 |

TABLE II

Range of concentrations of N-substituted amines required to kill 100% of nymphs and/or adults of the common scabies mite of cattle and sheep (*Psoroptes ovis*) exposed for 30 seconds in "tea bag" dipping tests.

| Compound Number | Concentration (%) |
|---|---|
| 6 | 0.001–0.005 |
| 7 | 0.001–0.005 |
| 8 | 0.001–0.005 |
| 15 | 0.001–0.005 |
| 18 | 0.001–0.005 |
| 20 | 0.001–0.005 |
| 22 | 0.001–0.005 |

TABLE III

Effects of N-substituted amines on the elimination of mites and scabs from the ears of rabbits infested with rabbit ear mites (*Psoroptes cuniculi*).

| Compound | Effect of Treatment Concentration % | | | |
|---|---|---|---|---|
| | 0.20 | 0.50 | 0.75 | 1.0 |
| 1 | B | — | — | C |
| 2 | — | — | B | D |
| 3 | B | D | D | D |
| 4 | — | — | D | D |
| 5 | B | C | D | D |
| 6 | — | — | B | D |
| 7 | B | C | D | D |
| 8 | — | — | D | D |
| 9 | — | B | B | B |
| 16 | — | B | C | B |

We claim:

1. A method of controlling scabies mites and other parasitic mites comprising applying to said mites a miticidally effective amount of a compound of the general formula

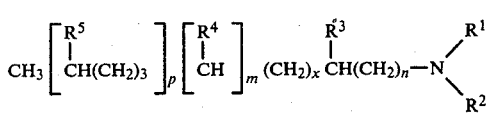

wherein $R^1$ and $R^2$ are selected individually from the group consisting of H, lower alkyl,

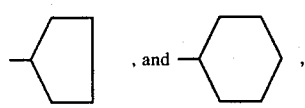

x is a number from 5 to 17, n is a number from 1 to 5, m and p are individually zero or 1, and $R^3$, $R^4$ and $R^5$ are individually H or lower alkyl.

2. A method of controlling scabies mites and other parasitic mites comprising applying to said mites a miticidally effected amount of a compound of the formula

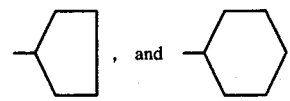

wherein $R^1$ and $R^2$ are selected individually from the group consisting of H, lower alkyl,

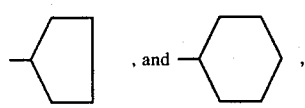

and x is a number from 10 to 17.

3. The method of claim 2 in which $R^1$ and $R^2$ are methyl and x is 15.

4. The method of claim 2 in which $R^1$ is methyl, $R^2$ is

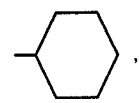

and x is 11.

5. A method of controlling scabies and other parasitic mites comprising applying to said mites a miticidally effective amount of a compound of the formula

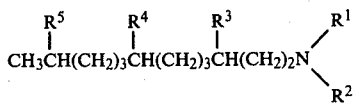

wherein $R^1$ and $R^2$ are selected individually from the group consisting of H, lower alkyl,

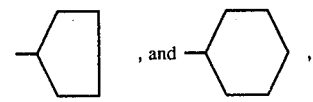

$R^3$, $R^4$, and $R^5$ are individually H or lower alkyl.

* * * * *

UNITED STATES PATENT AND TRADEMARK OFFICE
CERTIFICATE OF CORRECTION

PATENT NO. : 4,230,726

DATED : October 28, 1980

INVENTOR(S) : William F. Fisher, Malcolm J. Thompson, Fred C. Wright and William F. Robbins It is certified that error appears in the above—identified patent and that said Letters Patent is hereby corrected as shown below:

Column 4, line 64, "1.001%" should read -- 0.001% --.

Signed and Sealed this

Twenty-fourth Day of August 1982

[SEAL]

Attest:

Attesting Officer

GERALD J. MOSSINGHOFF

Commissioner of Patents and Trademarks